United States Patent [19]

Kuan

[11] Patent Number: 5,696,592
[45] Date of Patent: Dec. 9, 1997

[54] IMMERSIBLE APPARATUS FOR MEASURING LIGHT PENETRABILITY OF LIQUIDS

[76] Inventor: Ching Fu Kuan, No. 12, Alley 18, Lane 136, Er Jiu Rd., Ta Pu Lee, San Hsia, Taipei Hsien, Taiwan

[21] Appl. No.: 763,894

[22] Filed: Dec. 11, 1996

[51] Int. Cl.⁶ .................................................. G01N 21/00
[52] U.S. Cl. ........................... 356/436; 356/439; 356/440
[58] Field of Search .................................. 356/407, 409, 356/410, 419, 425, 44–45; 750/226

[56] References Cited

U.S. PATENT DOCUMENTS

| | | | |
|---|---|---|---|
| 4,637,729 | 1/1987 | Schoch | 356/410 |
| 4,682,895 | 7/1987 | Costello | 356/409 |
| 4,917,500 | 4/1990 | Lugos | 356/425 |
| 5,229,841 | 7/1993 | Taranowski et al. | 356/407 |
| 5,239,180 | 8/1993 | Clarke | 356/407 |

*Primary Examiner*—Frank G. Font
*Assistant Examiner*—Jason D. Vierra-Eisenberg
*Attorney, Agent, or Firm*—Bacon & Thomas

[57] ABSTRACT

An apparatus for measuring light penetrability of liquids, including: a water-tight, heat, compression and chemical resistant casing, a light source mounted inside the casing and controlled to alternately, emit light of different wavelengths, a controller mounted inside the casing for detecting light and converting detected light into electrical signals, and a light guide mounted inside the casing for guiding light from the light source to the controller through a liquid to be tested.

8 Claims, 3 Drawing Sheets

IMMERSIBLE APPARATUS FOR MEASURING LIGHT PENETRABILITY OF LIQUIDS

BACKGROUND OF THE INVENTION

The present invention relates to an apparatus for measuring light penetrability of liquids, and more particularly to such a light penetrability measuring apparatus which is simple in structure and practical in use and, which consumes less power supply.

A conventional light penetrability measuring apparatus is shown in FIG. 1, comprised of a light source A which can be a halogen lamp or xenon arc lamp, a color filer wheel assembly B disposed in front of the light source A and having color filters, which include a 660 nm red color filter, a 590 nm yellow color filter, a 560 nm green color filter and a 430 nm blue color filter, a colorless transparent water container C adapted for holding a test sample (for example, a dip dyeing liquid) to be measured, and a photo sensor D adapted for detecting light passing through the test sample and converting it into a corresponding electrical signal for further calculation, so that the light penetrability of the test sample can be known through a computing procedure. One drawback of this arrangement is that the light source consumes much energy. Another drawback of this arrangement is its heavy size. Still another object of this arrangement is that the light source as well as the color filters attenuate with use quickly. Furthermore, this arrangement is not suitable for high-temperature high-pressure on-line test because its electrical wiring is complicated.

SUMMARY OF THE INVENTION

The present invention has been accomplished to provide a light penetrability measuring apparatus which eliminates the aforesaid drawbacks. According to one aspect of the present invention, the apparatus is comprised of a water-tight casing, a light source mounted inside the casing and controlled to emit light of different wavelengths alternatively, a controller mounted inside the casing and adapted for detecting light and converting detected light into electrical signal, light guide means mounted inside the casing and adapted for guiding light from the light source to the controller through a liquid to be tested. According to another aspect of the present invention, the light source, the controller, and the light guide means are mounted inside the casing, and the casing is water-tight, heat-resistant, compression-resistant, and chemical resistant. According to still another aspect of the present invention, the light source is comprised of a plurality of light emitting diodes that emit light of different wavelengths, and switch means adapted for controlling the light emitting diodes separately.

DETAILED DESCRIPTION OF THE PREFERRED EMBODIMENTS

Figure 1:
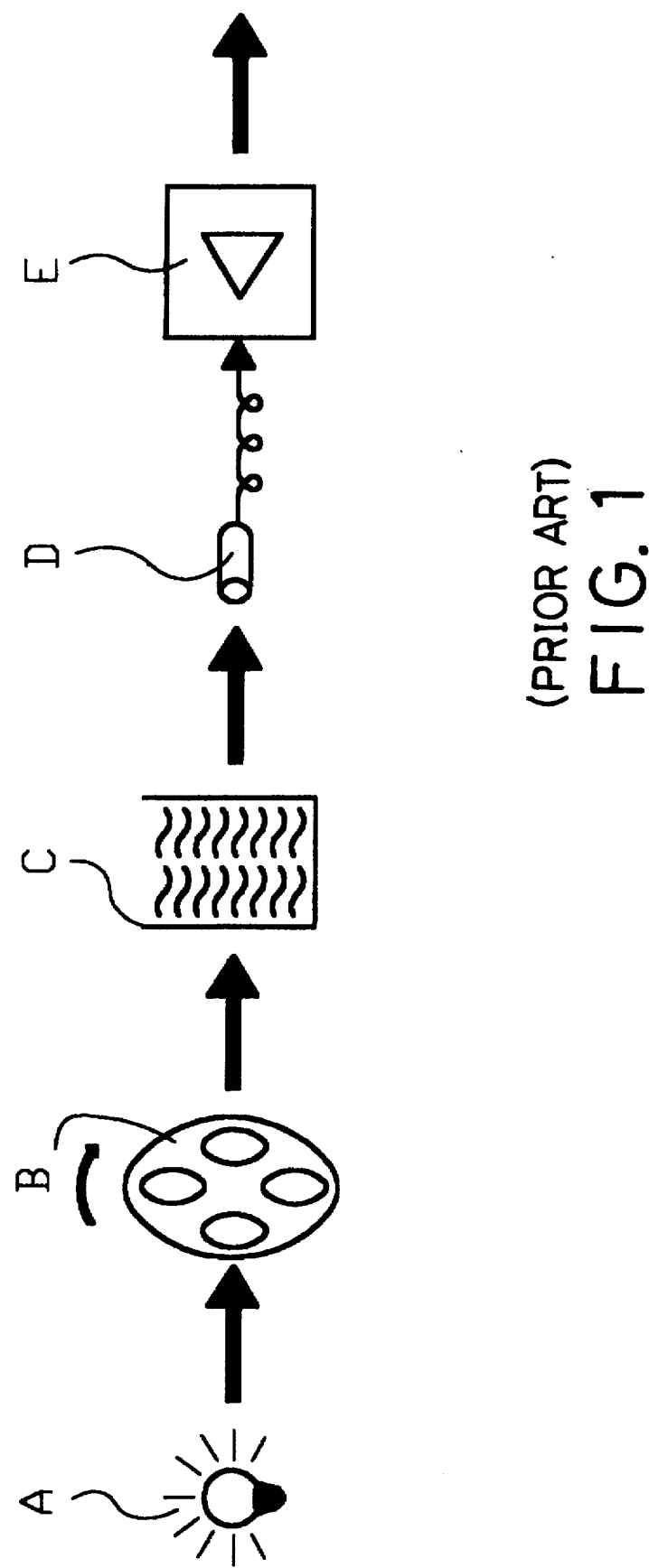
FIG. 1 is a schematic drawing showing the arrangement of a light penetrability measuring apparatus according to the prior art.
Figure 2:
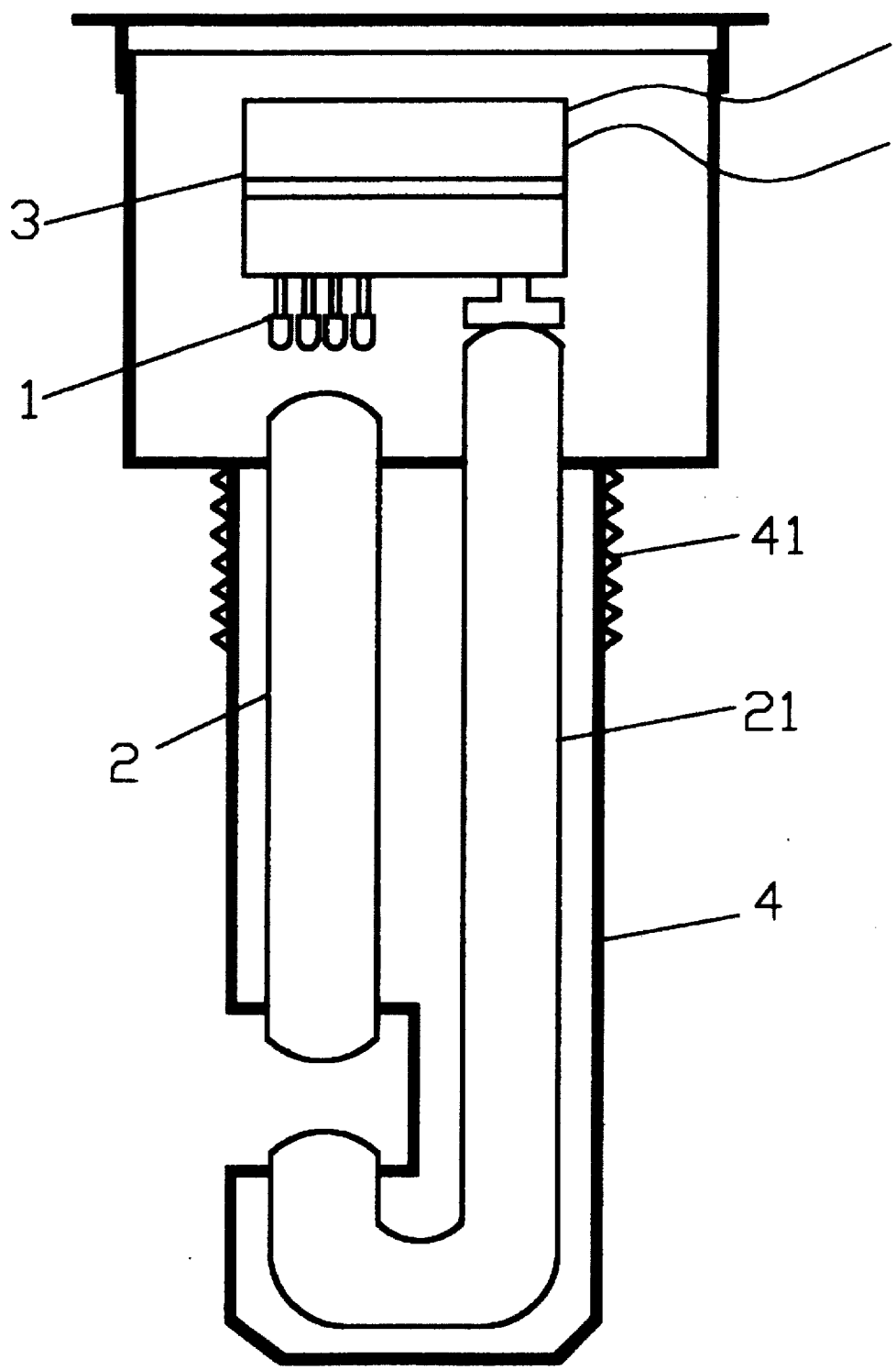
FIG. 2 is a plain view of an apparatus for measuring light penetrability of liquids according to one embodiment of the present invention.

Referring to FIG. 2, an apparatus for measuring light penetrability of liquids in accordance with the present invention, is generally comprised of a light source 1, a first light guide bar 2, a second light guide bar 21, a controller 3, and a casing 4. The light source 1, the light guide bars 2 and the controller 3 are mounted in the casing 4. The light source 1 is comprised of a plurality of LEDs (light emitting diodes), which are separately controlled to emit light of different wavelengths by a respective switch means.

The first light guide bar 2 is made from colorless transparent material, for example, optical fibers or optical glass, having one end (the top end) aimed at the aforesaid light source 1, and an opposite end (the bottom end) aimed at one end of the second light guide bar 21. The second light guide bar 21 is shaped like the English character "J", having one end (the top end) aimed at the controller 3 and an opposite end (the bottom end) aimed at one end of the first light guide bar 2 remote from the light source 3. The controller 3 is comprised of a photo sensor and an amplifier circuit, adapted for converting light into electrical signal, having communication interface means for connection to external apparatus. The casing 4 is water-tight, and can resist against heat at 135° C. or pressure at 3.5 kg/cm². When assembled, the first light guide bar 2 and the second light guide bar 21 are disposed in parallel; the bottom end of the second light guide bar 21 is longitudinally spaced from the bottom end of the first light guide bar 2 by a space in which test sample is filled for measuring. Further, the casing 4 has an outer thread 41 for mounting. Through the outer thread 41, the casing 4 can be installed in a water container designed for holding a test sample.

When in use, the casing 3 is fastened to the water container and dipped in the test sample, then the LEDs (for example, red, yellow, green and blue LEDs) of the light source 1 are alternatively turned on and off to respectively emit a particular wavelength of light. When a particular wavelength of light is produced from the light source 1, it passes through the first light guide bar 2, the test sample and the second light guide bar 21, and is then received by the controller 3. Upon receipt of light, the controller 3 immediately converts received light into a corresponding electrical signal. The electrical signal, after having been amplified, is sent to a peripheral equipment, which converts the signal into a digital value through a computing procedure, and therefore the concentration of the test sample, for example, a dip-dyeing liquor is measured.

Figure 3:
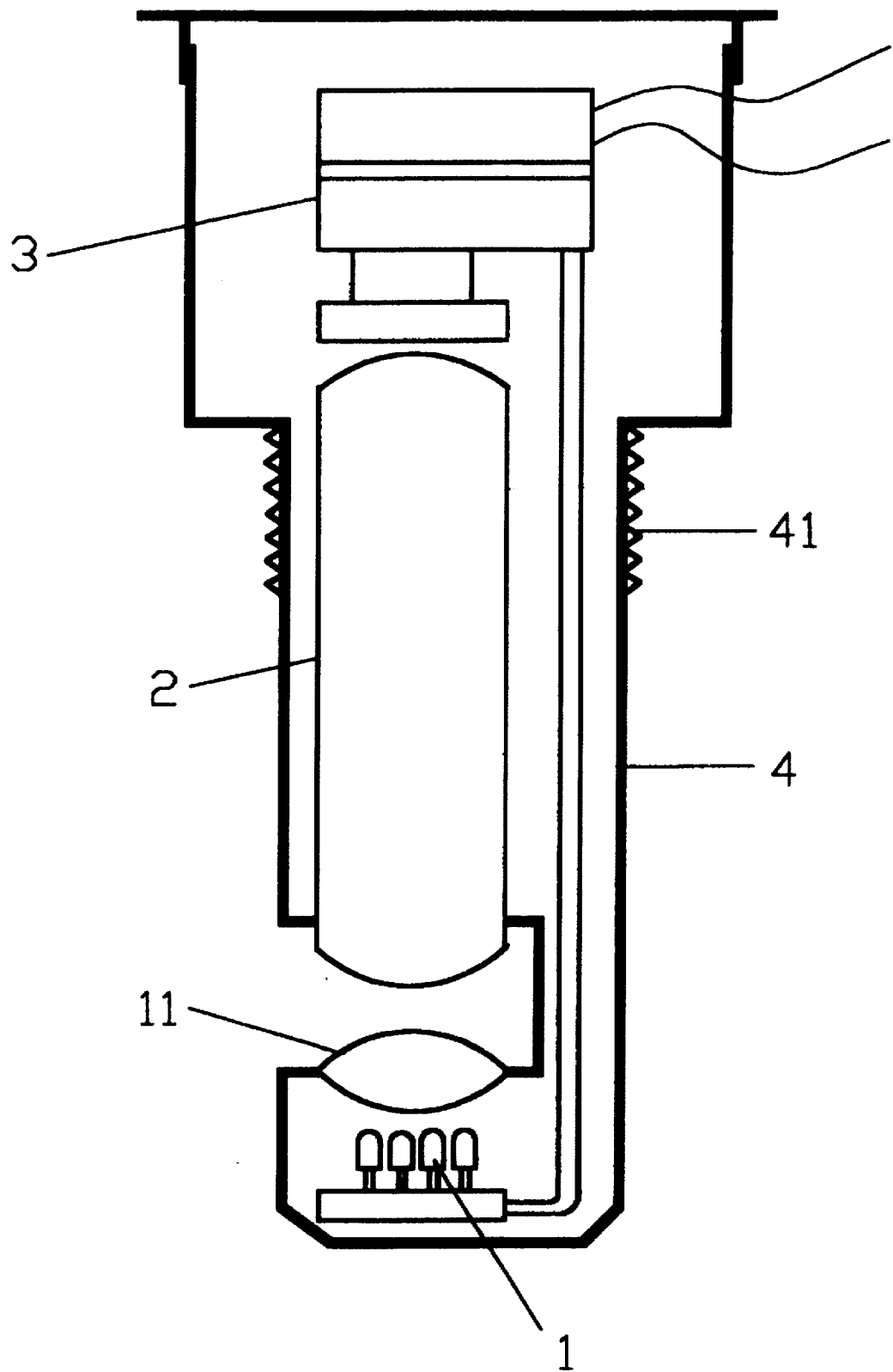
FIG. 3 is a plain view of an apparatus for measuring light penetrability of liquids according to a second embodiment of the present invention.

FIG. 3 shows an alternate form of the present invention. According to this alternate form, the light source 1 and the controller 3 are respectively mounted in the casing 4 at two opposite ends, the light guide bar 2 is disposed between the light source 1 and the controller 3, and a condensing lens 11 is disposed between the light source 1 and one end of the light guide bar 2 for focusing light from the light source 1 onto the light guide bar 2. This alternate form eliminates the aforesaid second light guide bar 21.

It is to be understood that the drawings are designed for purposes of illustration only, and are not intended as a definition of the limits and scope of the invention disclosed.

What the invention claimed is:

1. Apparatus for measuring light permeability of a liquid, comprising:

a) at least a first light guide bar having opposite first and second ends, a first end positioned in the liquid to be measured;

b) a light source having a plurality of light emitting diodes to emit light at a plurality of different wavelengths through the liquid and into the first end of the first light guide bar;

c) a controller connected to the light source such that the light source emits light one wavelength at a time, the controller having a photo sensor located adjacent to the second end of the first light guide bar to sense the light emanating from the second end of the first guide bar and to generate an electrical signal; and, d) a water tight casing enclosing the controller, the light source and the first light guide bar such that the first end of the first light guide bar is uncovered by the casing.

2. The apparatus of claim 1 further comprising a condensing lens located between the light source and the first light guide bar for focusing light from said light source to said first end of said first light guide bar.

3. The apparatus of claim 1 wherein said casing further comprises an outer thread portion.

4. The apparatus of claim 1 wherein said first light guide bar comprises optical fibers.

5. The apparatus of claim 1 wherein said first light guide bar comprises optical glass.

6. The apparatus of claim 1 wherein said casing is made from heat resistant, compression resistant, and chemical resistant material.

7. The apparatus of claim 1 further comprising a second light guide bar between the light source and the first end of the first light guide bar.

8. The apparatus of claim 7 wherein the first light guide bar has a substantially "J" shaped configuration.

* * * * *